United States Patent [19]

Benko et al.

[11] 4,409,219
[45] Oct. 11, 1983

[54] QUINOXALINE-1,4-DIOXIDE FODDER SUPPLIMENTS

[75] Inventors: Pál Benkő; Dániel Bózsing; Jámos Gundel; Károly Magyar, all of Budapest, Hungary

[73] Assignee: Egyt Gyogyszervegyeszeti Gyar, Budapest, Hungary

[21] Appl. No.: 266,300

[22] Filed: May 22, 1981

[30] Foreign Application Priority Data

May 23, 1980 [HU] Hungary .................. 1298/80

[51] Int. Cl.³ .................. C07D 403/12; C07D 403/6; C07D 341/12; A61K 31/495
[52] U.S. Cl. .................. 424/250; 544/120; 544/238; 544/295; 544/353; 542/413; 542/421; 542/439; 426/532
[58] Field of Search ............... 426/532; 544/353, 120, 544/238, 295; 424/250; 542/439, 413, 421

[56] References Cited

U.S. PATENT DOCUMENTS 4,100,284  7/1978  Cue .................. 544/353
4,225,604  9/1980  Hebky et al. .................. 544/353

FOREIGN PATENT DOCUMENTS 29924  10/1982  U.S.S.R. .

OTHER PUBLICATIONS

Ried et al., Chem. Abstracts 51, 8109c, (1957).

*Primary Examiner*—Mark L. Berch
*Attorney, Agent, or Firm*—Karl F. Ross; Herbert Dubno

[57] ABSTRACT

The invention relates to new quinoxaline-1,4-derivatives of the general formula (I) and biologically acceptable salts thereof,

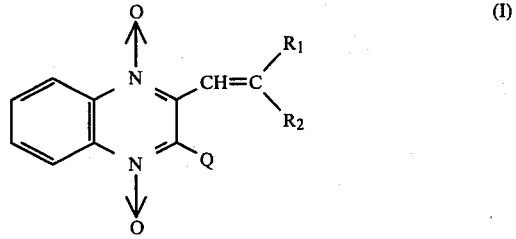

wherein
Q is a hydrogen atom or a methyl group,
$R_1$ represents a hydrogen atom, a cyano, lower alkanoyl or nitro group or a halogen atom,
$R_2$ stands for cyano, lower alkanoyl, or a group of the general formula $—COOR_3$, $—CONR_4R_5$ or $—CO—NH—NR_4R_5$, and
$R_3$ represents a hydrogen atom or a $C_{1-18}$ alkyl, $C_{6-12}$ aryl or $C_{6-10}$aryl-($C_{1-4}$alkyl) group optionally substituted by a halogen atom or a hydroxy group, whereby the aromatic ring of the said groups may optionally contain 1–3 identical or different substituents selected from the group consisting of lower alkyl or alkoxy, amino, nitro, halogen and/or hydroxy,
$R_4$ is a hydrogen atom or a $C_{1-18}$ alkyl, a lower alkenyl, a lower alkynyl, a lower cycloalkyl, $C_{6-10}$ aryl, $C_{6-10}$ aryl-($C_{1-4}$ alkyl) group optionally substituted by a halogen atom or a hydroxy group, whereby the aryl ring of the said groups may optionally contain 1–3 identical or different substituents selected from the group consisting of lower alkoxy, lower alkyl, amino, nitro, halogen and/or hydroxy substituents, a lower alkylcarbonyl, a lower alkylsulfonyl or a $C_{6-10}$ arylsulfonyl group optionally substituted by an amino or a lower alkyl group; or a mono- or bicyclic heteroarylsulfonyl group, or
$R_4$ and $R_5$ represent, together with the adjacent nitrogen atom, a 5 or 6 membered heterocyclic group optionally substituted by a further nitrogen or oxygen atom,
with the proviso that if Q represents hydrogen and $R_2$ stands for carboxy, $R_1$ may denote only other than hydrogen. Moreover, the invention relates to a process for the preparation of the above compounds and fodder concentrates, fodder additives or fodders containing the said compounds.

The new compounds of the general formula (I) possess weight-gain increasing and antibacterial effects and can be used to advantage in the animal husbandry.

8 Claims, No Drawings

QUINOXALINE-1,4-DIOXIDE FODDER SUPPLIMENTS

The invention relates to new quinoxaline-1,4-dioxide derivatives, a process for the preparation thereof and a composition containing these compounds, particularly a fodder concentrate or a fodder.

It is known that certain quinoxaline-1,4-dioxide derivatives possess antimicrobial and weight-gain increasing effect. Schiff bases of 2-formyl-quinoxaline-1,4-dioxides are described in U.S. Pat. No. 3,371,090. Other quinoxaline-1,4-dioxide derivatives are mentioned in Belgian Pat. No. 764,088 and in British patent specification No. 1,670,935.

According to the present invention there are provided new quinoxaline-1,4-dioxide derivatives of the formula I and biologically acceptable salts thereof,

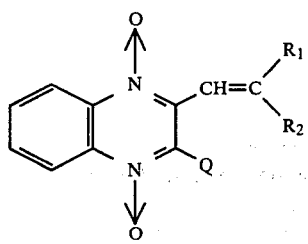
(I)

wherein
Q is hydrogen or methyl,
$R_1$ is hydrogen, cyano, lower alkanoyl or nitro or a halogen atom,
$R_2$ is cyano, lower alkanoyl, or a group of the formula —$COOR_3$—, —$CONR_4R_5$ or —CO—NH—$NR_4R_5$, and
$R_3$ is hydrogen or $C_{1-18}$ alkyl, $C_{6-12}$ aryl or $C_{6-10}$ aryl-($C_{1-4}$ alkyl) optionally substituted by a halogen atom or a hydroxy group, whereby the aromatic ring of the said groups may also contain 1-3 identical or different substituents selected from the group consisting of lower alkyl or alkoxy, amino, nitro, halogen and/or hydroxy,
$R_4$ is hydrogen atom or $C_{1-18}$ alkyl, lower alkenyl, lower alkynyl, lower cycloalkyl, $C_{6-10}$ aryl, $C_{6-10}$ aryl-($C_{1-4}$ alkyl) optionally substituted by a halogen atom or a hydroxy group, whereby the aryl ring of the said groups may also contain 1-3 identical or different substituents selected from the group consisting of lower alkoxy, lower alkyl, amino, nitro, halogen and/or hydroxy substituents; a lower alkylcarbonyl, a lower alkylsulfonyl or a $C_{6-10}$ arylsulfonyl group optionally substituted by an amino or a lower alkyl group; or a mono- or bicyclic heteroarylsulfonyl group;
$R_5$ is hydrogen, hydroxyethyl, dodecyl, phenyl, p-amino-phenylsulfonyl or methoxycarbonyl; or
$R_4$ and $R_5$ represent, together with the adjacent nitrogen atom, a 5 or 6 membered heterocyclic group optionally substituted by a further nitrogen or oxygen atom,
but where Q represents hydrogen and $R_2$ is for carboxy, $R_1$ is other than hydrogen.

The term "lower" refers to hydrocarbon groups containing 1-4 carbon atoms. The term "halogen atom" encompasses all the four halogen atoms, i.e. fluorine, chlorine, bromine or iodine. The term "lower alkanoyl" stands for the acid residues of alkanoic acids containing 1-4 carbon atoms, e.g. acetyl, propionyl or butyryl. The term "$C_{1-18}$ alkyl group" represents straight-chain or branched saturated aliphatic hydrocarbon groups containing 1-18 carbon atoms, e.g. methyl, ethyl, n-propyl, isopropyl, n-butyl, n-hexyl, n-dodecyl. The term "$C_{6-10}$ aryl group" includes the phenyl and naphthyl groups. The "$C_{6-10}$ aryl-($C_{1-4}$ alkyl) group" is preferably benzyl, $\beta$-phenylethyl, $\alpha$-phenylethyl or $\beta,\beta$-diphenylethyl. The aryl ring of the above compounds can contain 1-3 identical or different substituents, such as lower alkoxy, amino, nitro, halogen or hydroxyl (e.g. 2-, 3- or 4-methoxy, 2,3-, 2,4-, 2,5-, 3,4- or 2,6-dimethoxy, 2,3,5, 2,4,5 or 2,4,6-trimethoxy, 2,3, 2,4, 2,5 or 3,5-dimethyl, 2-chloro-6-methyl, 3,5-dichlorophenyl). The term "lower alkoxy" refers to straight-chain or branched alkoxy groups containing 1-4 carbon atoms (e.g. methoxy, ethoxy, n-propoxy). The hydroxyalkyl group is preferably the 2-hydroxyethyl group. The "lower alkynyl groups" can be straight-chain or branched and contain 2-5 carbon atoms (e.g. propynyl, 1,1-dimethylpropyn-2-yl). The "lower cycloalkyl group" may contain 3-6 carbon atoms (e.g. cyclopentyl cyclohexyl). The preferred representatives of the "lower alkoxycarbonyl group" are the methoxycarbonyl and ethoxycarbonyl groups. The "lower alkylsulfonyl groups" contain the above, defined alkyl groups (e.g. methylsulfonyl, ethylsulfonyl). The "arylsulfonyl group optionally substituted by an amino or a lower alkyl group" can be e.g. p-amino-phenylsulfonyl or p-methyl-phenylsulfonyl group. The heterocyclic ring of the "heteroarylsulfonyl group" can a monocyclic or bicyclic, optionally substituted heteroaromatic group which contains one or two nitrogen, sulfur and/or oxygen atoms (e.g. pyridyl, thiazolyl, isothiazolyl, pyrimidinyl, pyridazinyl, pyrazinyl, furyl, imidazolyl, oxazolyl, quinolyl, isoquinolyl). The substituent of the said heterocyclic ring can be e.g. lower alkyl (methyl or ethyl), halogen (such as chlorine or bromine), hydroxy, lower alkoxy (e.g. methoxy, ethoxy), nitro and/or amino.

$R_4$ and $R_5$ may represent, together with the adjacent nitrogen atom, a 5 or 6 membered, optionally substituted heterocyclic group which may contain a further nitrogen or oxygen (e.g. pyrrolidino, piperidino, morpholino, piperazino or N-substituted piperazino, e.g. N-methyl, N-ethyl, N-phenyl- or N-benzyl-piperazino group).

The compounds of the formula I, wherein $R_2$ represents carboxy groups, can form salts with bases. The invention relates particularly to the biologically acceptable salts of the compounds of the formula I. The alkali salts (e.g. sodium or potassium salts), the alkaline-earth salts (e.g. calcium or magnesium salts), the ammonium salts and the salts formed with biologically acceptable organic bases (such as triethylamine, dimethylamine, dimethylaniline, ethanolamine) are particularly preferred.

A particularly preferred representative of the compounds of the formula I is the $\beta$-(2-quinoxalinyl-1,4-dioxide)-acrylic ethyl ester.

The following compounds are further preferred representatives of the compounds of the formula I:
$\beta$-(2-quinoxalinyl-1,4-dioxide)-acrylic methyl ester,
$\alpha$-cyano-$\beta$-(2-quinoxalinyl-1,4-dioxide)-acrylic methyl ester,
$\alpha$-acetyl-$\beta$-(2-quinoxalinyl-1,4-dioxide)-acrylic methyl ester, α-cyano-β-(2-quinoxalinyl-1,4-dioxide)-acrylic-2'-pyridyl amide,
β-(2-quinoxalinyl-1,4-dioxide)-acrylic dodecyl amide,
β-(2-quinoxalinyl-1,4-dioxide)-acrylic anilide,
β-(2-quinoxalinyl-1,4-dioxide)-acrylic morpholide,
β-(2-quinoxalinyl-1,4-dioxide)-acrylic-N-benzyl-piperazide,
β-(2-quinoxalinyl-1,4-dioxide)-acrylic-(p-aminobenzenesulfonic amide).
β-(2-quinoxalinyl-1,4-dioxide)-acrylic-(2-methoxycarbonyl)-hydrazide,
β-(2-quinoxalinyl-1,4-dioxide)-acrylic-(2-hydroxyethyl)-amide.

According to a further feature of the invention there is provided a process for the preparation of the new quinoxaline-1,4-dioxide derivatives of the formula I, wherein Q, $R_1$ and $R_2$ have the above defined meanings, and salts thereof, characterized by a. dehydrating a compound of the formula II

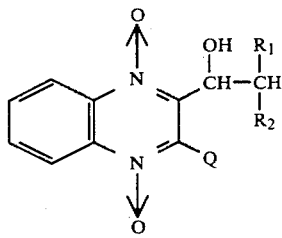

wherein Q, $R_1$ and $R_2$ have the above defined meanings, or b. to prepare compounds of the formula I, wherein $R_2$ is cyano, lower alkanoyl or a group of the general formula —COOR$_3$, and $R_1$, Q and $R_3$ have the same meanings as above, reacting a compound of the formula (III)

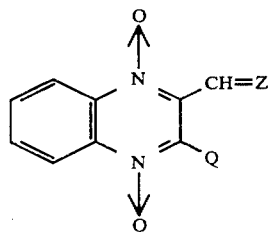

wherein Z represents an oxygen atom or two lower alkoxy groups and Q has the same meanings as above, with a compound of the formula IV $$R_6\text{—}CH_2\text{—}CO\text{—}R_7 \qquad (IV)$$

wherein $R_6$ is carboxy, cyano, lower alkanoyl, nitro or halogen and $R_7$ is lower alkoxy, amino or hydroxy, or c. to prepare a compound of the formula I, wherein $R_2$ stands for a group of the formula —CONR$_4$R$_5$ or —CO—NH—NR$_4$R$_5$ and Q, $R_1$, $R_4$ and $R_5$ have the above-defined meanings, reacting a compound of the formula V

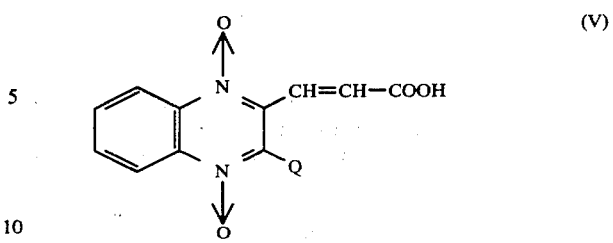

wherein Q has the same meanings as above, or a reactive derivative thereof, with an amine of the formula VI $$R_4\text{—}NH\text{—}R_5 \qquad (VI)$$

wherein $R_4$ and $R_5$ has the above-defined meanings, or with a hydrazine of the formula VIA

or with a salt thereof, or d. oxidizing a compound of the formula VII

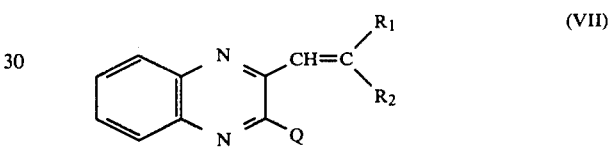

wherein Q, $R_1$ and $R_2$ have the same meanings as above, and, if desired, transesterifying a compound of the formula I thus-obtained, wherein $R_2$ stands for a group of the formula —COOR$_3$ and $R_3$ is a lower alkyl; or, if desired, esterifying a compound of the formula I thus obtained, wherein $R_2$ stands for a carboxy group; or, if desired, saponifying a compound of the formula I thus-obtained, wherein $R_2$ represents a group of the general formula —COOR$_3$ and $R_3$ has the same meanings as above except hydrogen; and, if desired, converting a compound of the formula I thus-obtained into a biologically acceptable salt or setting free a base of the formula I from its salt.

According to the variant a. of the process according to the invention a compound of the formula II is dehydrated. The reaction is carried out in a known way. The dehydration is preferably performed in alkaline or acidic medium. As an alkaline medium, pyridine is suitable, and as an acidic medium, hydrochloric, oxalic, phosphoric, or p-toluenesulfonic acid can be used. One proceeds preferably in the presence of a catalyst (e.g. iodine). The reaction is carried out between 10° C. and the boiling point of the reaction mixture.

According to the variant b. of the process according to the invention a compound of the formula I, wherein $R_2$ stands for cyano, lower alkanoyl or a group of the formula —COOR$_3$ (wherein Q, $R_1$ and $R_3$ have the above defined meanings) is prepared by reacting a compound of the formula III with a compound of the formula IV. The reaction is preferably carried out in the presence of a base. Organic bases (such as pyridine, triethylamine, piperidine) or inorganic bases (e.g. alkali or alkaline-earth hydroxides, alkali or alkaline-earth carbonates or bicarbonates, preferably sodium hydroxide or potassium hydroxide) can be used for this purpose. Preferably 1-1.8, particularly 1-1.1 moles of the compound of the formula IV can be used relative to 1 mole of the compound of the formula III. The reaction is preferably carried out in an inert solvent or dilutent. As reaction medium, e.g. ethers (such as diethyl ether, dioxane or tetrahydrofuran), lower dialkylformamides (such as dimethylformamide), aliphatic or aromatic hydrocarbons (such as hexane, heptane, benzene, toluene or xylene), halogenated aliphatic or aromatic hydrocarbons (such as chloroform, methylene chloride, hydrocarbon tetrachloride, chlorobenzene), nitrated hydrocarbons (such as nitromethane nitrobenzene), lower alkyl nitriles (such as acetonitrile), heteroaromatic compounds (such as pyridine, quinoline), aliphatic alkanols (such as isopropanol), or mixtures thereof can be used. The reaction is preferably carried out between 40° C. and the boiling point of the reaction mixture.

As starting material of the formula IV, different —CH-acid compounds, such as lower malonic monoesters, malonic monoamides, lower malonic dialkylesters, cyanoacetic acid, lower alkyl esters of the cyanoacetic acid or cyanoacetic amide can be used.

According to the variant c. of the process according to the invention compounds of the formula I, wherein $R_2$ represents a group of the general formula —$CONR_4R_5$ or —$CONHNR_4R_5$ and $R_4$, $R_5$, $R_1$ and Q have the above-defined meanings, are prepared by reacting a compound of the formula V or a reactive derivative thereof with an amine of the formula VI, with a hydrazine of the formula VIA or with a salt thereof.

As reactive derivatives of the carboxylic acids of the formula V preferably esters (e.g. lower alkyl esters), reactive aryl esters (such as p-nitrophenyl, p-chlorophenyl ester), acetic halides (such as acyl chloride) or mixed anhydrides can be used. It is preferable to use as reactive derivative the mixed anhydride of a carboxylic acid of the formula V formed with a haloformiate of the formula VIII

Hal—$COOR_8$  (VIII)

wherein Hal is halogen and $R_8$ represents $C_{1-10}$ alkyl or $C_{6-10}$ aryl. The reaction is preferably carried out in an inert organic solvent and in the presence of an acid binding agent. For this purpose the solvents and bases mentioned in connection with the variant b. are suitable. The reaction is generally performed between 0° C. and room temperature. It is preferable to proceed by forming the reactive derivative of the compound of the formula V at 0°-10° C., then reacting the product thus-obtained, after or without isolation, with an amine of the formula VI or with a hydrazine of the formula VIA or with the salt thereof at about room temperature.

As salts of the amine of the formula VI or of the hydrazine of the formula VIA, e.g. the hydrochloride or the addition salts formed with other suitable acids can be used.

When using a free carboxylic acid of the formula V, the reaction is preferably carried out in the presence of a dehydrating agent (e.g., N,N-dicyclohexylcarbodiimide).

According to the variant d. of the process according to the invention a compound of the formula VII is oxidized. The oxidation is carried out by known methods, e.g. by reacting with peracids (such as peracetic, perbenzoic, m-chloroperbenzoic acid) or with hydrogen peroxide in the presence of vanadic acid, sodium vanadate, vanadium pentoxide or sodium tungstate. One proceeds at a temperature between 40°-100° C.

The compounds of the formula I, wherein $R_2$ represents lower alkyl, can be converted into other esters of the formula I by transesterification.

The transesterification is carried out in a known way. One can proceed e.g. by reacting the ester used as starting material with an excess of the transesterifying alkanol in the presence of a base (e.g. alkali hydroxide) or an acid (e.g. hydrochloric acid).

The transesterification of the compounds of the formula I, wherein $R_2$ represents —$COOR_3$ and $R_3$ is hydrogen, can be carried out by known methods. The carboxylic acid is reacted with the corresponding alkanol in the presence of an acidic catalyst (e.g. hydrochloric or p-toluenesulfonic acid). The esterification can be carried out also with alkyl halides or diazomethane.

The saponification of the esters of the formula I, wherein $R_2$ represents a group of the formula —$COOR_3$, wherein $R_3$ has the same meanings as above except hydrogen, can be performed in a known way. One proceeds e.g. so that the ester is reacted with a base (e.g. alkali hydroxide, alkali carbonate, alkali bicarbonate, alkali alcoholate), and the alkali salt thus-obtained is treated with an acid to liberate the free carboxylic acid of the formula I.

The compounds of the formula I, wherein $R_2$ is carboxy, can be converted into biologically acceptable salts or can be liberated from their salts. The salt formation is carried out in a known way, that is by reacting a carboxylic acid of the formula I with the corresponding base in the presence of an inert solvent.

The compounds of the formula II and V used as starting materials can be prepared in the way described in the scientific literature (Zsur. Obscs. Khim. 28, 1378 1958; DOS No. 2,354,252). The starting materials of the formula III are known (British patent specification No. 1,308,370).

The starting materials of the formula IV, VI and VIA are commercial products. The starting compounds of the formula VII can be prepared in the way described in J. Chem. Soc. 1956, 2052 or Dutch patent specification No. 7,401,966.

The new compounds according to the invention possess weight-gain increasing and antibacterial effects and can be used therefore advantageously in animal husbandry.

The high antibacterial effect of wide spectrum of the compounds of the present invention makes them suitable to be used for the prevention or treatment of systemic or local bacterial infections. These compounds are effective against various grampositive and gram-negative bacteria, particularly against the following strains: Enterobacteriaceae, e.g. Escherichia, particularly *E. coli*, Pseudomonadaceae, e.g. *Pseudomonas aeruginosa*, Micrococcaceae, e.g. *Staphylococcus aureus*.

The minimal inhibiting concentration of the compounds of the formula I against the above bacteria varies between 0.5 and 128 γ/ml.

The weight-gain increasing effect of the new compounds according to the invention is illustrated by the following tests. Pigs served as test animals. Each dose was administered to groups consisting of 6 pigs and each test was repeated thrice with each animal. The fodder used for the feeding of the animals contained 50 mg/kg of the quinoxaline-1,4-dioxide derivative of the general formula I. The animals were masted under identical conditions, and each group of animals consumed the same amount of the same fodder except the active ingredient content. The control group was fed with the same amount of fodder containing no active ingredient. The results obtained with the compound of the Example 1 are shown in Table 1.

TABLE 1

| Test compound | The average of the daily increase in weight-gain, related to the control group | The amount of the fodder resulting 1 kg of weight-gain increase, related to the control group |
|---|---|---|
| β-(2-Quinoxalinyl-1,4-dioxide)-acrylic acid ethyl ester | 134.4% | 78.7% |
| Control group (without ingredient) | 100.0% | 100.0% |

The above data prove that the animals fed with a fodder containing the new compounds according to the present invention show a considerably higher weight-gain increase than the animals of the control group. The same weight-gain increase can be achieved with a significantly smaller amount of fodder, which means that the utilization of the fodder is improved in this way.

A further advantage of the compounds according to the invention is that they are evacuated much easier from the organism of the animals than the known quinoxaline-1,4-dioxide derivatives, i.e. their withdrawal period is shorter, which is of great importance in animal husbandry.

The toxicity of the compounds of the formula I on domestic animals is so low that they are partically considered atoxical.

According to a further feature of the invention there are provided veterinary compositions containing an effective amount of a compound of the formula I, wherein Q, R$_1$ and R$_2$ have the above defined meanings, or biologically acceptable salts thereof, together with an inert, solid or liquid carrier or diluent.

The compositions according to the invention can be prepared in the forms generally used in the veterinary science, e.g. in tablets, dragees, bolus, etc. These compositions may contain usual inert carriers or diluents and can be produced by methods generally applied in the pharmaceutical industry.

According to a further feature of the invention there are provided fodder concentrates, fodder additives or fodders containing an effective amount of a compound of the formula I, wherein Q, R$_1$ and R$_2$ have the above defined meanings, or a biologically acceptable salt thereof, together with an edible solid or liquid carrier or additive.

As carrier, any substance of vegetable or animal origin applied for foddering is suitable. As carrier e.g. wheat meal, rice-bran, wheat bran, soy flour, maize-germ flour, bone meal, lucerne flour, soy grits, meat meal, fish meal, maize meal or the mixtures thereof can be used. A particularly preferred carrier is a fiber-free green-plant fodder concentrate of increased protein content, e.g. VEPEX ®.

As additives, e.g. silica, wetting agent, antioxidant, starch, dicalcium phosphate, calcium carbonate, sorbic acid, etc. can be used. As wetting agent, non-toxic oils, particularly soy, maize or mineral oils are used. Various alkylene glycols are also preferable as wetting agents. As starch, maize, wheat or potato starch can be used.

According to a preferred embodiment of the invention a fodder concentrate containing 0.01–95% by weight of an active ingredient of the formula I, 0.01–40% by weight of calcium hydrophosphate, 0.01–23% by weight of calcium carbonate, 0.01–12% by weight of bone meal and/or lucerne meal, 2–98% by weight of carrier, 0.2–1.6% by weight of silica, 0.1–0.4% by weight of antioxidant and 1–8% by weight of wetting agent are prepared, e.g. by admixing the components. If desired, the concentrate may contain 10–25% by weight of starch and different vitamines, at most in an amount of 3%.

The fodder concentrates can be used for the feeding of animals after dilution, while the fodders can be fed up directly by the animals.

The fodder according to the invention can be used for the feeding of different domestic animals, such as pig, cattle, sheep, poultry, etc., particularly pig.

The amount of the ingredient in the composition according to the invention can be varied within wide ranges. The fodder concentrate contains generally about 5–80% by weight, preferably about 10–80% by weight, particularly 20–50% by weight, of a compound of the formula I. The amount of the compound of the formula I in the fodder additive is about 1–100 ppm, particularly 10–50 ppm.

The invention is illustrated by the following Examples of non-limiting character:

EXAMPLE 1

15.85 g (0.12 moles) of malonic monoethyl ester are admixed with 40 ml of pyridine. 19 g (0.1 mole) of 2-formylquinoxaline-1,4-dioxide are added under stirring, then 0.86 g (0.01 mole) of piperidine are dropped into it. The reaction mixture is warmed for 4 hours, cooled and poured onto icy water. The separated product is filtered off, washed first with water then with acetone. 19.5 g (75%) of β-(2quinoxalinyl-1,4-dioxide)-acrylic acid ester are obtained.

M.p.: 190°–191° C.

EXAMPLE 2

A mixture of 13 g (0.05 moles) of β-(2-quinoxalinyl-1,4-dioxide)-acrylic acid ethyl ester, 70 ml of methanol and 7 ml of 1 N aqueous sodium hydroxide solution is warmed for half an hour at 50° C., then the mixture is cooled, and the separated product is filtered off. 8.9 g (73%) of β-(2-quinoxalinyl-1,4-dioxide)-acrylic acid methyl ester are obtained.

M.p.: 207°–208° C.

EXAMPLE 3

A mixture of 19 g (0.1 mole) of 2-formyl-quinoxaline-1,4-dioxide, 9.9 g (0.1 mole) of cyanoacetic methyl ester, 160 ml of isopropanol and 3.5 ml of a 10% aqueous sodium hydroxide solution is warmed at 60° C. for 2 hours. The mixture is cooled to 5° C., the separated product is filtered off. 22.1 g (82%) of α-cyano-β-(2-quinoxalinyl-1,4-dioxide)-acrylic acid methyl ester are obtained. The red crystals melt at 198°–99° C.

EXAMPLE 4

When reacting 2-formyl-quinoxaline-1,4-dioxide and cyanoacetic ethyl ester in the way as described in Example 3, α-cyano-β-(2quinoxalinyl-1,4-dioxide)-acrylic acid ethyl ester is obtained. Yield: 85.5%.

M.p.: 160°–161° C.

EXAMPLE 5

A mixture of 11.6 g (0.05 moles) of β-(2-quinoxalinyl-1,4-dioxide)-acrylic acid, 65 ml of dimethylformamide, 65 ml of ethylacetate and 5.06 g (0.05 moles) of triethylamine is stirred for half an hour. Then it is cooled to 0° C., and 5.5 g (0.05 moles) of ethyl chloroformate are added dropwise. The mixture is cooled and kept below 5° C. for 2 hours, then 9.3 g (0.05 moles) of dodecyl amine are added and the mixture is allowed to warm up to room temperature. After cooling to 5° C. the separated product is filtered off and recrystallized from dimethylformamide. 16.2 g (81%) of β-(2-quinoxalinyl-1,4-dioxide)-acrylic dodecyl amide are obtained.

M.p.: 197°–198° C.

EXAMPLE 6

When reacting β-(2-quinoxalinyl-1,4-dioxide)-acrylic acid, ethyl chloroformate and 1,1-dimethyl-propyn-2-yl amide in the way as described in Example 5, 61% of β-(2-quinoxalinyl-1,4-dioxide)-acrylic-(1,1-dimethyl-propyn-2-yl) amide are obtained.

M.p.: 210° C.

EXAMPLE 7

When reacting β-(2-quinoxalinyl-1,4-dioxide)-acrylic acid, buthyl chloroformate and aniline in the way as described in Example 5, 60% of β-(2quinoxalinyl-1,4-dioxide)-acrylic anilide are obtained.

M.p.: 245°–246° C.

EXAMPLE 8

When reacting β-(2-quinoxalinyl-1,4-dioxide)-acrylic acid, methyl bromoformate and N-benzyl-piperazine in the way as described in Example 5, 89% of β-(2-quinoxalinyl-1,4-dioxide)-acrylic-N-benzyl-piperazide are obtained.

M.p.: 195°–196° C.

EXAMPLE 9

When reacting β-(2-quinoxalinyl-1,4-dioxide)-acrylic acid, methyl chloroformate and morpholine in the way as described in Example 5, 95% of β-(2-quinoxalinyl-1,4-dioxide)-acrylic morpholide are obtained.

M.p.: 221°–222° C.

EXAMPLE 10

When reacting β-(2-quinoxalinyl-1,4-dioxide)-acrylic acid, ethyl chloroformate and 3,4,5-trimethoxy aniline, 97% of β-(2-quinoxalinyl-1,4-dioxide)-acrylic-3,4,5-trimethoxy-anilide are obtained.

M.p.: 225° C.

EXAMPLE 11

One proceeds in the way as described in Example 5, with the difference that ethanol amine is used, instead of dodecyl amine. 92% of β-(2quinoxalinyl-1,4-dioxide)-acrylic-2'-hydroxy-ethyl amide are obtained.

M.p.: 213°–214° C.

EXAMPLE 12

One proceeds in the way as described in Example 5, with the difference that 2,6-dimethyl-aniline is used, instead of dodecyl amine. 98% of β-(2-quinoxalinyl-1,4-dioxide)-acrylic-2,6-dimethyl anilide are obtained.

M.p.: 229°–230° C.

EXAMPLE 13

One proceeds in the way as described in Example 9, with the difference that piperidine is used, instead of morpholine. 97% of β-(2-quinoxalinyl-1,4-dioxide)-acrylic piperidine are obtained.

M.p.: 201°–202° C.

EXAMPLE 14

One proceeds in the way as described in Example 5, with the difference that methyl carbazate is used, instead of dodecyl amine. 76% of β-(2-quinoxalinyl-1,4-dioxide)-acrylic-2-methoxycarbonyl hydrazide are obtained.

M.p.: 234°–235° C.

EXAMPLE 15

One proceeds in the way as described in Example 5, with the difference that p-amino-benzenesulfonic amide is used, instead of dodecyl amine. 83% of β-(2quinoxalinyl-1,4-dioxide)-acrylic-(p-amino-benzenesulfonic) amide are obtained.

M.p.: 278° C. (decomp.)

EXAMPLE 16

A mixture of 9.5 g (0.05 moles) of 2-formyl-quinoxaline-1,4-dioxide, 5.8 g (0.05 moles) of acetoacetic methyl ester, 120 ml of isopropanol and 2 ml of a 10% aqueous sodium hydroxide solution is allowed to stand at room temperature for 5 hours. Then it is cooled to 5° C. and the separated product is filtered off. 10.8 g (75%) of α-acetyl-β-(2-quinoxalinyl-1,4-dioxide)-acrylic acid methyl ester are obtained.

M.p.: 159°–160° C.

EXAMPLE 17

One proceeds in the way as described in Example 16, with the difference that cyanoacetic amide is used, instead of acetoacetic methyl ester. 75% of α-cyano-β-(2-quinoxalinyl-1,4-dioxide)-acrylic amide are obtained.

M.p.: 212° C.

EXAMPLE 18

5.9 g (0.02 moles) of 2-(β-hydroxy-2-quinoxalinyl-methylene-1,4-dioxide)-malonic acid are dissolved in 40 ml of pyridine, and the solution is warmed for an hour at 70° C. Then it is cooled and the separated product is filtered off. 4.1 g (90%) of β-(2-quinoxalinyl-1,4-dioxide)-acrylic acid are obtained.

M.p.: 227°–230° C.

EXAMPLE 19

On starting from α-cyano-β-hydroxy-(2quinoxalinyl-1,4-dioxide)-propionic methyl ester and proceeding as described in Example 18, 85% of α-cyano-β-(2-quinoxalinyl-1,4-dioxide)-acrylic acid methyl ester are obtained.

M.p.: 198°–199° C.

EXAMPLE 20

One proceeds as described in Example 18, with the difference that β-hydroxy-β-(2-quinoxalinyl-1,4-dioxide)-propionic dodecyl amide is used as starting material. 87% of β-(2-quinoxalinyl-1,4-dioxide)-acrylic dodecyl amide are obtained.

M.p.: 198°–198.5° C.

EXAMPLE 21

When reacting β-hydroxy-β-(2-quinoxalinyl-1,4-dioxide)-propionic-N-benzenepiperazide in the way as described in Example 18, 92% of β-(2-quinoxalinyl-1,4-dioxide)-acrylic-N-benzenepiperazide are obtained.
M.p.: 194°–195° C.

EXAMPLE 22

When reacting β-hydroxy-β-(2-quinoxalinyl-1,4-dioxide)-propionic-2'-methoxycarbonyl hydrazide in the way as described in Example 18, 89% of β-(2-quinoxalinyl-1,4-dioxide)-acrylic-2-methoxycarbonyl hydrazide are obtained.
M.p.: 234°–235° C.

EXAMPLE 23

When reacting β-hydroxy-β-(2-quinoxalinyl-1,4-dioxide)-propionic-(p-amino-benzenesulfonic) amide in the way as described in Example 18, 89% of β-(2-quinoxalinyl-1,4-dioxide)-acrylic-(p-aminobenzenesulfonic) amide are obtained.
M.p.: 278°–279° C. (decomp.)

EXAMPLE 24

Preparation of a concentrate "A"

37 kg of wheat-bran are admixed with 30 kg of β-(2-quinoxalinyl-1,4-dioxide)-acrylic-(p-aminobenzenesulfonic) amide, 3 kg of propylene glycol are sprayed to it, then 2 kg of sorbic acid, 0.5 kg of sodium chloride and 2 kg of fish meal are added and the mixture is stirred for 5 minutes.

Into an other apparatus 120 kg of lucerne flour and 210 kg of greenplant concentrate (VEPEX®) are weighed, then 6 kg of propylene glycol are sprayed to it. Thereafter 37 kg of the concentrate "A" are added, under stirring, 5.5 kg of propylene glycol are sprayed, finally 85 kg of starch are added.

EXAMPLE 25

350 kg of pre-milled soy flour are weighed into a mixer, and 2.7 kg of soy oil are added, under stirring, and stirring is continued until the product becomes oil-free. Thereafter 8.2 kg of β-(2-quinoxalinyl-1,4-dioxide)-acrylic acid ethyl ester are added, and the mixture is stirred further until it becomes completely homogeneous. To the mixture 8.2 kg of soy oil are added and it is homogenized.

EXAMPLE 26

1.2 kg of β-(2-quinoxalinyl-1,4-dioxide)-acrylic acid methyl ester are added to 90 kg of maize flour under stirring. In the meantime 6.2 kg of propylene glycol are sprayed into the system. Finally 3.2 kg of dicalcium phosphate are added, and the mixture is homogenized.

EXAMPLE 27

20 kg of lucerne flour and 30 kg of VEPEX® are stirred for 1.5 minutes. 2 kg of maize oil are sprayed uniformly into the system while the following components are added as well: 5 kg of α-cyano-β-(2-quinoxalinyl-1,4-dioxide)-acrylic acid methyl ester, 20 kg of maize starch, 5 kg of the above active ingredient, 0.7 kg of silica, 1.3 kg of ascorbic acid, 17 kg of maize starch and 5 kg of the above active ingredient. Then the mixture is stirred further for 5 minutes.

EXAMPLE 28

One proceeds in the way described in Example 26, except that butylene glycol is used as wetting agent, instead of soy oil.

EXAMPLE 29 a. 35 kg of potato starch are admixed with 29 kg of α-acetyl-β-(2-quinoxalinyl-1,4-dioxide)-acrylic acid methyl ester. 0.5 kg of mineral oil are sprayed into the mixture, then 2 kg of sorbic acid, 3.8 kg of silica and 0.9 kg of calcium propionate are added, and the mixture is stirred for 2 minutes.

b. 42 kg of fish flour and 220 kg of rye bran are admixed, 6.3 kg of mineral oil are sprayed into the system, then 38 kg of a mixture described in paragraph a., 105 kg of maize flour, 37 kg of a mixture described in paragraph a. and 90 kg of maize flour are added, finally 6 kg of mineral oil are sprayed into it.

EXAMPLE 30

80 kg of wheat bran, 9 kg of β-(2-quinoxalinyl-1,4-dioxide)-acrylic-(2-methoxycarbonyl) hydrazide, 2.3 kg of calcium carbonate, 0.1 kg of α-tocoferol and 0.3 kg of calcium propionate are homogenized with 3 kg of propylene glycol.

EXAMPLE 31

100 kg of soy flour, 5.5 kg of β-(2quinoxalinyl-1,4-dioxide)-acrylic morpholide and 2.3 kg of butylene glycol are homogenized.

EXAMPLE 32

90 kg of soy flour, 11 kg of β-(2-quinoxalinyl-1,4-dioxide)-acrylic acid ethyl ester, 0.9 kg of silica, 3.2 kg of soy oil and 0.2 kg of calcium propionate are homogenized.

EXAMPLE 33

One proceeds as described in Examle 24, with the difference that clinoptilolite is used instead of starch.

What we claim is:
1. A compound of the formula (I)

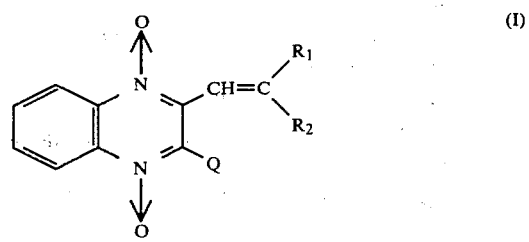

wherein
Q is hydrogen or methyl;
$R_1$ is hydrogen, cyano, lower alkanoyl, nitro or halogen;
$R_2$ is cyano, lower alkanoyl, or a group of the formula —$COOR_3$, —$CONR_4R_5$, or —$CONHNR_4R_5$;
$R_3$ is hydrogen, $C_1$ to $C_{18}$ alkyl, $C_6$ to $C_{10}$ aryl, or $C_6$ to $C_{10}$aryl-($C_1$ to $C_4$alkyl) which latter can be substituted with a halogen or a hydroxy group, and the aromatic ring of the said aryl groups can contain 1 to 3 substituents selected from the group consisting of lower alkyl or alkoxy, amino, nitro, halogen and hydroxy;

R$_4$ is hydrogen, C$_1$–C$_{18}$alkyl, lower alkenyl, lower alkynyl, lower cycloalkyl, C$_6$ to C$_{10}$ aryl, C$_6$ to C$_{10}$aryl-(C$_1$ to C$_4$alkyl) which can be substituted by a halogen or a hydroxy group, and the aromatic ring of said aryl groups can contain 1 to 3 substituents selected from the group consisting of lower alkoxy, lower alkyl, amino, nitro, halogen, and hydroxy, a lower alkylcarbonyl, a lower alkylsulfonyl, or a C$_6$ to C$_{10}$ arylsulfonyl group which can be substituted by an amino or a lower alkyl group, or a mono- or bicyclic heterocyclic sulfonyl group wherein the heterocyclic group is selected from the group consisting of pyridyl, thiazolyl, isothiazolyl, pyrimidinyl, pyridazinyl, pyrazinyl, furyl, imidazolyl, oxazolyl, quinolyl, and isoquinolyl and wherein the heterocyclic group is unsubstituted or substituted by lower alkyl, halogen, hydroxy, lower alkoxy, nitro or amino;

R$_5$ is hydrogen, hydroxyethyl, dodecyl, 1,1-dimethyl-propyn-2-yl, phenyl, 3,4,5-trimethoxy-phenyl, 2,6-dimethyl-phenyl, 2-pyridyl, p-amino-phenylsulfonyl, or methoxycarbonyl; or R$_4$ and R$_5$ together with the adjacent nitrogen atom form a pyrolidino, piperidino, morpholino, piperazino, N-methyl-piperazino, N-ethyl-piperazino, N-phenyl-piperazino, or N-benzyl-piperazino, or in the case wherein R$_2$ is carboxy, a pharmaceutically acceptable basic carboxylate salt thereof, but when Q is hydrogen and R$_2$ is carboxy, R$_1$ is different from hydrogen.

2. A compound of the formula (I)

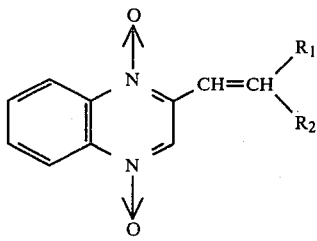

wherein
R$_1$ is hydrogen, acetyl or cyano;
R$_2$ is a group of the formula —COOR$_3$, —CONR$_4$R$_5$, or —CONHNR$_4$R$_5$;
R$_3$ is methyl or ethyl;
R$_4$ is hydrogen;
R$_5$ is hydrogen, hydroxyethyl, dodecyl, phenyl, p-aminophenyl-sulfonyl or methoxycarbonyl; or
R$_4$ and R$_5$ together with the adjacent nitrogen atom form a morpholino, piperidino or N-benzyl-piperazino group.

3. β-(2-Quinoxalinyl-1,4-dioxide)-acrylic ethyl ester.

4. The compound of the formula (I) defined in claim 1 selected from the group consisting of:
(a) β-(2-quinoxalinyl-1,4-dioxide)-acrylic acid ethyl ester;
(b) β-(2-quinoxalinyl-1,4-dioxide)-acrylic acid methyl ester;
(c) α-cyano-β-(2-quinoxalinyl-1,4-dioxide)-acrylic acid methyl ester; and
(d) β-(2-quinoxalinyl-1,4-dioxide)-acrylic-2,6-dimethylanilide.

5. The compound of the formula (I) defined in claim 1 selected from the group consisting of:
(a) β-(2-quinoxalinyl-1,4-dioxide)-acrylic ethyl ester;
(b) β-(2-quinoxalinyl-1,4-dioxide)-acrylic methyl ester;
(c) α-cyano-β-(2-quinoxalinyl-1,4-dioxide)-acrylic methyl ester;
(d) α-cyano-β-(2-quinoxalinyl-1,4-dioxide)-acrylic ethyl ester;
(e) β-(2-quinoxalinyl-1,4-dioxide)-acrylic dodecyl amide;
(f) β-(2-quinoxalinyl-1,4-dioxide)-acrylic-(1,1-dimethyl-propyn-2-yl)amide;
(g) β-(2-quinoxalinyl-1,4-dioxide)-acrylic amide;
(h) β-(2-quinoxalinyl-1,4-dioxide)-acrylic-N-benzyl-piperazide;
(i) β-(2-quinoxalinyl-1,4-dioxide)-acrylic morpholide;
(j) β-(2-quinoxalinyl-1,4-dioxide)-acrylic-3,4,5-trimethoxy-anilide;
(k) β-(2-quinoxalinyl-1,4-dioxide)-acrylic-2-hydroxyethylamide;
(l) β-(2-quinoxalinyl-1,4-dioxide)-acrylic-2,6-dimethylanilide;
(m) β-(2-quinoxalinyl-1,4-dioxide)-acrylic-piperidide;
(n) β-(2-quinoxalinyl-1,4-dioxide)-acrylic-methoxycarbonyl-hydrazide;
(o) β-(2-quinoxalinyl-1,4-dioxide)-acrylic-(p-aminobenzenesulfonic)-amide;
(p) α-acetyl-β-(2-quinoxalinyl-1,4-dioxide)-acrylic methyl ester;
(q) α-cyano-β-(2-quinoxalinyl-1,4-dioxide)-acrylic amide; and
(r) α-cyano-β-(2-quinoxalinyl-1,4-dioxide)-acrylic-2-pyridyl-amide.

6. An antimicrobial or weight-gain increasing veterinary composition containing a compound as defined in claim 1, together with a suitable insert, solid or liquid carrier or diluent.

7. A fodder concentrate or fodder of antimicrobial or weight-gain increasing effect containing an effective amount of a compound as defined in claim 1 or a biologically acceptable carboxylate salt thereof together with a suitable inert, solid or liquid carrier or diluent.

8. A process for increasing the weight-gain and the fodder-utilization of animals, characterized by feeding the said animals with a fodder as claimed in claim 7.

* * * * *